US008675946B2

(12) United States Patent
Sakaguchi et al.

(10) Patent No.: US 8,675,946 B2
(45) Date of Patent: Mar. 18, 2014

(54) X-RAY DIAGNOSIS APPARATUS AND IMAGE PROCESSING APPARATUS

(75) Inventors: Takuya Sakaguchi, Shioya-gun (JP); Kunio Shiraishi, Otawara (JP); Masayuki Nishiki, Otawara (JP); Kyojiro Nambu, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1110 days.

(21) Appl. No.: 12/629,351

(22) Filed: Dec. 2, 2009

(65) Prior Publication Data
US 2010/0142792 A1 Jun. 10, 2010

(30) Foreign Application Priority Data

Dec. 5, 2008 (JP) .................................. 2008-311267

(51) Int. Cl.
*A61B 6/03* (2006.01)
(52) U.S. Cl.
CPC ....................................... *A61B 6/03* (2013.01)
USPC ........................................................... 382/132
(58) Field of Classification Search
USPC ........................... 382/128–132; 600/424–427
See application file for complete search history.

(56) References Cited

U.S. PATENT DOCUMENTS 5,293,574 A * 3/1994 Roehm et al. ................. 378/98.2
7,492,947 B2 2/2009 Nanbu
2005/0074158 A1 * 4/2005 Kaufhold et al. ............. 382/132
2007/0083114 A1 4/2007 Yang et al.
2008/0279476 A1 11/2008 Rongen et al.

FOREIGN PATENT DOCUMENTS

| CN | 1640113 A | 7/2005 |
| JP | 1-273487 | 11/1989 |
| JP | 7-322240 A | 12/1995 |
| JP | 8-255238 A | 10/1996 |
| JP | 2006-255217 A | 9/2006 |
| JP | 2007-330522 | 12/2007 |
| WO | WO 02/086821 | 10/2002 |

OTHER PUBLICATIONS

Masayuki Nishiki, et al., "Method for reducing noise in X-ray images by averaging pixels based on the normalized difference with the relevant pixel." Radiol Phys Technol, 2008, 8 pages.

(Continued)

*Primary Examiner* — Toan Ton
*Assistant Examiner* — John Corbett
(74) *Attorney, Agent, or Firm* — Oblon, Spivak, McClelland, Maier & Neustadt, L.L.P.

(57) ABSTRACT

When a plurality of X-ray images in a time sequence is stored in an image data storing unit (25), a marker coordinate detecting unit (26a) detects coordinates of a stent marker in each X-ray image, and a motion vector calculating unit (26b) calculates, with coordinates of the stent marker detected in a first frame as reference coordinates, a motion vector of the coordinates of the stent marker detected in each X-ray image of a second and subsequent frames with respect to the reference coordinates. Then, a filter application range determining unit (26c) moves and determines an application range of a smoothing filter in each X-ray image based on the motion vector, and the filtered image generating unit (26d) generates a filtered image by performing a process by the smoothing filter between application ranges determined in a process target image and a reference image.

7 Claims, 6 Drawing Sheets

(56) References Cited

OTHER PUBLICATIONS

Chinese Office Action issued Jan. 14, 2011, in Patent Application No. 200910253121.6.
Office Action issued Apr. 3, 2012, in Japanese Patent Application No. 2008-311267 with English translation.
Jovan G. Brankov, et al., "4D Smoothing of Gated SPECT Images Using a Left-Ventricle Shape Model and a Deformable Mesh", 2004 IEEE Nuclear Science Symposium Conference Record (IEEE Cat. No. 04CH37604), vol. 5, XP-002568738, Oct. 16-22, 2004, pp. 2845-2848.

A. Pizurica, et al., "Image De-Noising in the Wavelet Domain Using Prior Spatial Constraints", Image Processing and its Applications, Conference Publication No. 465, vol. 1, Jul. 13, 1999, pp. 216-219.

* cited by examiner

APPLICATION RANGE MOVED

APPLICATION RANGE MOVED (A)

(B)

X-RAY DIAGNOSIS APPARATUS AND IMAGE PROCESSING APPARATUS

CROSS-REFERENCE TO RELATED APPLICATIONS

This application is based upon and claims the benefit of priority from the prior Japanese Patent Application No. 2008-311267, filed on Dec. 5, 2008; the entire contents of which are incorporated herein by reference.

BACKGROUND OF THE INVENTION

1. Field of the Invention

The present invention relates to an X-ray diagnosis apparatus and an image processing apparatus 2. Description of the Related Art Conventionally, a smoothing filter such as a recursive filter that performs a smoothing process between a plurality of frames in a time sequence is widely used as a method for reducing noise in an X-ray image.

Specifically, the recursive filter is a filter that reduces high frequency noise by adding pixel values of pixels constituting a past frame on which a predetermined weighting is performed to pixel values of pixels constituting a frame as a process target (for example, see JP-A 2007-330522 (KO-KAI)).

Moreover, recently, in an intravascular interventional treatment that is widespread as a treatment method for an infarct site, a treatment using a stent is performed by a doctor who sees an X-ray image. However, in the intravascular interventional treatment, the treatment time may be long, so that an X-ray image (fluoroscopic image) is radiographed with the minimum X-ray dose to be radiated to a patient. Therefore, noise increases on an X-ray image to be seen by a doctor. Thus, reduction of noise on a fluoroscopic image by the smoothing filter is important in the intravascular interventional treatment.

The above described conventional technology has a problem in that the noise reducing effect by the smoothing filter is not always ensured.

In other words, when the recursive filter is applied to an X-ray image of an organ such as a heart that beats, which is radiographed in a time sequence, a target object to be filtered moves between a plurality of frames, so that motion blur occurs. Specially, in the intravascular interventional treatment for an infarct site of a heart, if the above described filter is applied, motion blur of a stent occurs in a fluoroscopic image by heartbeats.

In this manner, the recursive filter cannot be applied strongly to an X-ray image radiographed a moving object, so that noise cannot be reduced significantly.

The present invention has been achieved to solve the problem in the above conventional technology, and it is an object of the present invention to provide an X-ray diagnosis apparatus and an image processing apparatus capable of always ensuring a noise reducing effect by a smoothing filter.

SUMMARY OF THE INVENTION

According to an aspect of the present invention, an X-ray diagnosis apparatus includes an image data generating unit that generates X-ray images in a time sequence by detecting an X-ray that is radiated from an X-ray tube and is transmitted through an subject; a feature-point-position detecting unit that detects a position of a feature point included in a predetermined target object from at least a first image and a second image included in the X-ray images generated in a time sequence by the image data generating unit; an application range determining unit that determines an application range of a smoothing filter in the first image and the second image based on a position of the feature point in the first image and a position of the feature point in the second image detected by the feature-point-position detecting unit; and a filtering unit that performs a smoothing filter process by using the first image and the second image based on the application range of the smoothing filter determined by the application range determining unit.

According to another aspect of the present invention, an image processing apparatus includes a feature-point-position detecting unit that detects a position of a feature point included in a predetermined target object from at least a first image and a second image included in a plurality of medical images generated in a time sequence; an application range determining unit that determines an application range of a smoothing filter in the first image and the second image based on a position of the feature point in the first image and a position of the feature point in the second image detected by the feature-point-position detecting unit; and a filtering unit that performs a smoothing filter process by using the first image and the second image based on the application range of the smoothing filter determined by the application range determining unit.

DETAILED DESCRIPTION OF THE INVENTION

Exemplary embodiments of an X-ray diagnosis apparatus and an image processing apparatus according to the present invention are explained in detail below with reference to the accompanying drawings. In the following, the embodiments are explained taking a case of applying the present invention to the X-ray diagnosis apparatus.

Figure 1:
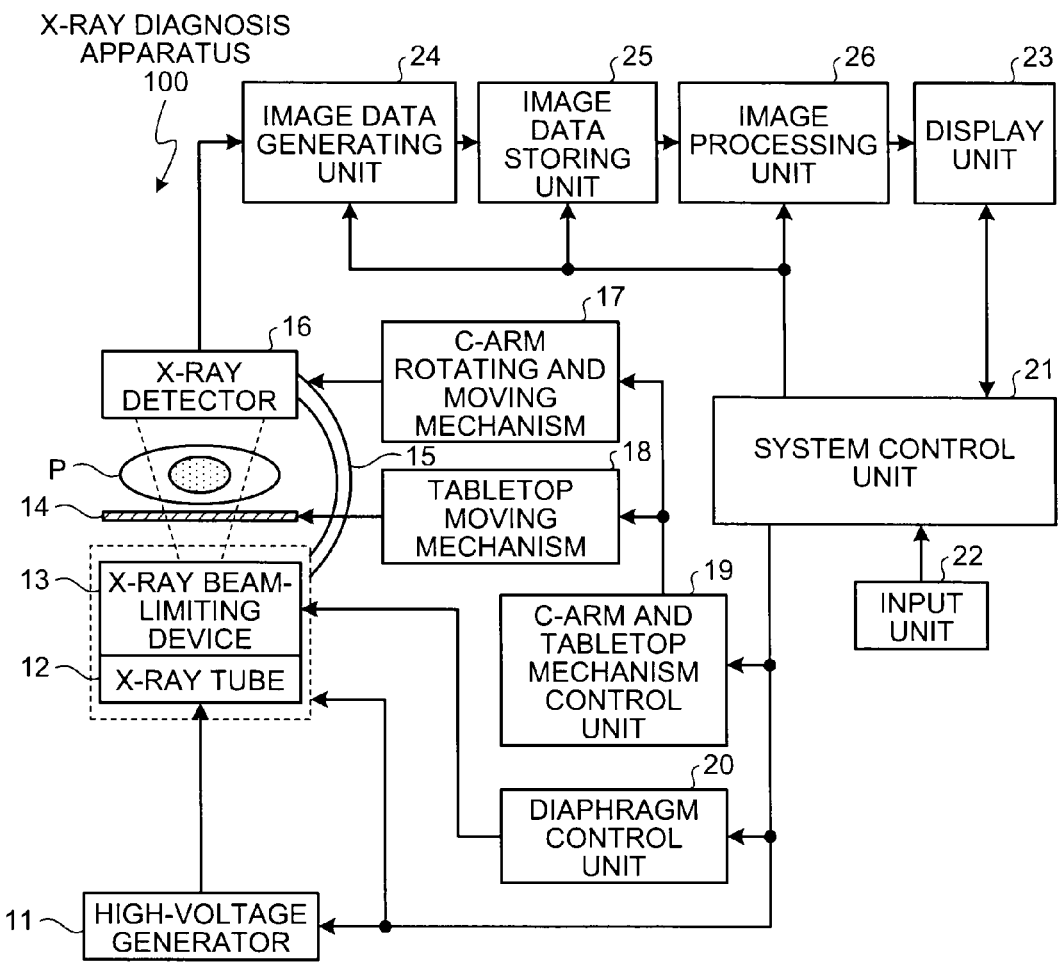
FIG. 1 is a diagram for explaining a configuration of an X-ray diagnosis apparatus according to a first embodiment.

First, a configuration of the X-ray diagnosis apparatus according to a first embodiment is explained. FIG. 1 is a diagram for explaining the configuration of the X-ray diagnosis apparatus according to the first embodiment.

As shown in FIG. 1, an X-ray diagnosis apparatus 100 in the present embodiment includes a high-voltage generator 11, an X-ray tube 12, an X-ray beam-limiting device 13, a tabletop 14, a C arm 15, an X-ray detector 16, a C-arm rotating and moving mechanism 17, a tabletop moving mechanism 18, a C-arm and tabletop mechanism control unit 19, a diaphragm control unit 20, a system control unit 21, an input unit 22, a display unit 23, an image data generating unit 24, an image data storing unit 25, and an image processing unit 26.

The high-voltage generator 11 is a device that generates a high voltage and supplies the generated high voltage to the X-ray tube 12. The X-ray tube 12 is a device that generates an X-ray by using the high voltage supplied from the high-voltage generator 11. Specifically, the high-voltage generator 11 performs the adjustment of an X-ray dosage radiated to a subject P and the ON/OFF control of X-ray radiation to the subject P by adjusting the voltage supplied to the X-ray tube 12.

The X-ray beam-limiting device 13 is a device that narrows an X-ray generated by the X-ray tube 12 to be selectively radiated to a region of interest of the subject P. For example, the X-ray beam-limiting device 13 includes slidable four diaphragm blades, and narrows the X-ray generated by the X-ray tube 12 by sliding the diaphragm blades and radiates it to the subject P.

The tabletop 14, on which the subject P is placed, is arranged on a bed (not shown).

The X-ray detector 16 is a device in which X-ray detecting elements for detecting an X-ray transmitted through the subject P are aligned in a matrix manner. Each X-ray detecting element converts the X-ray transmitted through the subject P to an electric signal and accumulates it, and sends the accumulated electric signal to the image data generating unit 24, which will be described later.

The C-arm 15 is an arm that supports the X-ray tube 12, the X-ray beam-limiting device 13, and the X-ray detector 16, so that "the X-ray tube 12 and the X-ray beam-limiting device 13" and the X-ray detector 16 are arranged with the C-arm 15 on opposite sides of the subject P.

The C-arm rotating and moving mechanism 17 is a device that rotates and moves the C arm 15, and the tabletop moving mechanism 18 is a device that moves the tabletop 14.

The C-arm and tabletop mechanism control unit 19 performs the rotation adjustment and the movement adjustment of the C arm 15 and the movement adjustment of the tabletop 14 by controlling the C-arm rotating and moving mechanism 17 and the tabletop moving mechanism 18.

The diaphragm control unit 20 controls a radiation range of an X-ray by adjusting the opening of the diaphragm blades of the X-ray beam-limiting device 13.

The image data generating unit 24 generates an X-ray image by using an electric signal converted from an X-ray that transmits through the subject P by the X-ray detector 16 and stores the generated X-ray image in the image data storing unit 25. Specifically, the image data generating unit 24 performs a current-voltage conversion, an analog-digital (A/D) conversion, and a parallel-serial conversion on the electric signal received from the X-ray detector 16 to generate an X-ray image.

The image data storing unit 25 stores therein an X-ray image generated by the image data generating unit 24.

The image processing unit 26 is a processing unit that performs various image processing on an X-ray image stored in the image data storing unit 25. Specifically, the image processing unit 26 performs a smoothing filter process for reducing noise on the X-ray image, which will be described in detail later.

The input unit 22 includes a mouse, a keyboard, a button, a trackball, a joystick, and the like for an operator such as a doctor and an engineer who operates the X-ray diagnosis apparatus 100 inputting various commands, and transfers the command received from the operator to the system control unit 21.

The display unit 23 includes a monitor for displaying a graphical user interface (GUI) for receiving a command from an operator via the input unit 22, an X-ray image stored in the image data storing unit 25, an X-ray image subjected to the image processing by the image processing unit 26, and the like.

The system control unit 21 controls the operation of the entire X-ray diagnosis apparatus 100. Specifically, the system control unit 21 performs the adjustment of an X-ray dosage and the ON/OFF control of X-ray radiation, the adjustment of the rotation and the movement of the C arm 15, and the movement adjustment of the tabletop 14 by controlling the high-voltage generator 11, the C-arm and tabletop mechanism control unit 19, and the diaphragm control unit 20 based on a command from an operator that is transferred from the input unit 22.

Moreover, the system control unit 21 performs the control of the image generating processing in the image data generating unit 24 and the image processing in the image processing unit 26 based on a command from an operator. Furthermore, the system control unit 21 controls to display the GUI for receiving a command from an operator, an X-ray image stored in the image data storing unit 25, an X-ray image subjected to the image processing by the image processing unit 26, and the like on the monitor of the display unit 23.

When performing an intravascular interventional treatment using a stent with a stent strut and a balloon on an infarct site in a cardiac blood vessel of the subject P, the X-ray diagnosis apparatus 100 in the present embodiment performs a fluoroscopic radiography of an X-ray image for the infarct site in which the stent is inserted as a region of interest in a time sequence based on a command from an operator. In the present embodiment, explanation is given for the case where two X-ray impermeable metals are attached to both sides of the balloon portion of the stent as stent markers; however, the present invention can be applied to the case where one X-ray impermeable metal is attached to a middle of the balloon portion of the stent as the stent marker.

In other words, the X-ray diagnosis apparatus 100 in the present embodiment radiates a low-dose X-ray from the X-ray tube 12 to the infarct site of the subject P subjected to the intravascular interventional treatment and detects an X-ray transmitted through the subject P by the X-ray detector 16, thereby storing X-ray images (fluoroscopic images) that are sequentially generated in a time sequence in the image data storing unit 25. In the following, a fluoroscopic image stored in the image data storing unit 25 is described as an X-ray image. Moreover, in the following, a plurality of fluoroscopic images generated in a time sequence is described as "a first frame, a second frame, . . . " in a time sequence in some cases.

Figure 2:
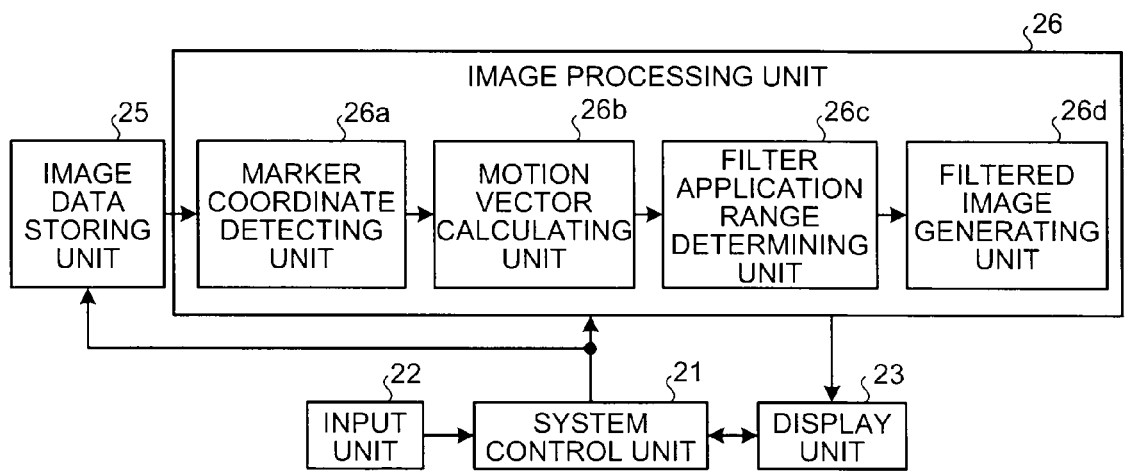
FIG. 2 is a diagram for explaining a configuration of an image processing unit according to the first embodiment.
Figure 4:
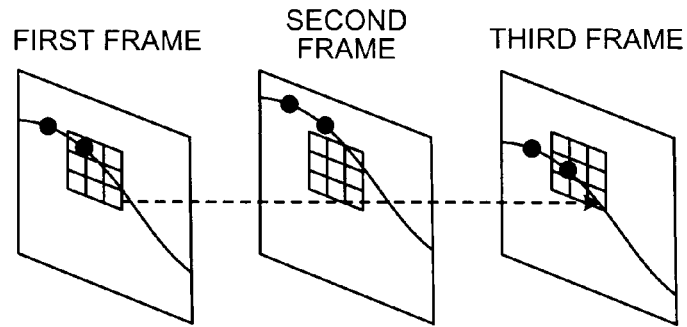
FIGS. 4 and 5 are diagrams for explaining a filter application range determining unit.
Figure 4:
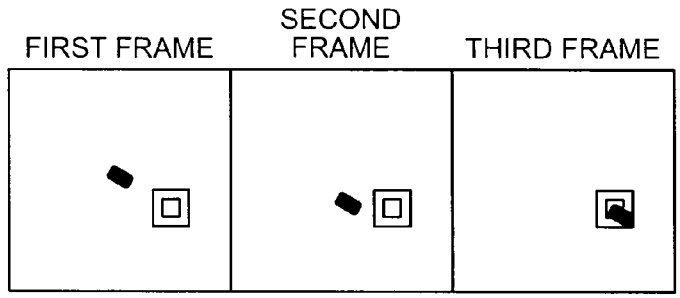
Figure 5:
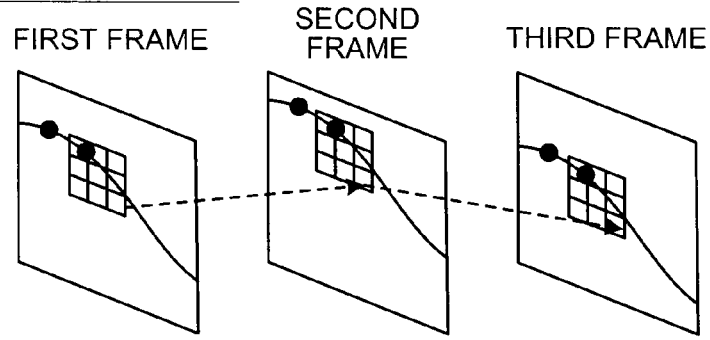
Figure 5:
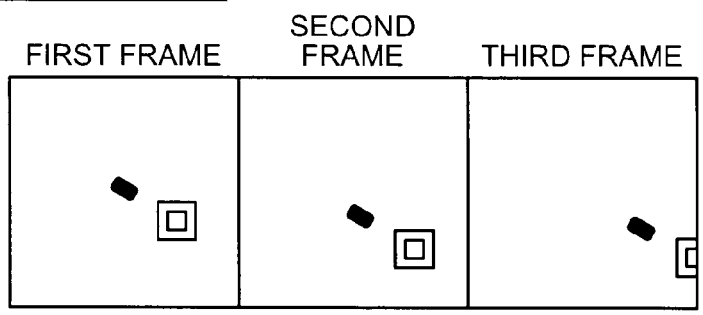

The X-ray diagnosis apparatus 100 in the present embodiment is mainly characterized in that the noise reducing effect by the smoothing filter can be always ensured by performing a process by the image processing unit 26 that is explained in detail below with reference to FIG. 2 to FIG. 5. FIG. 2 is a diagram for explaining a configuration of an image processing unit according to the first embodiment, FIG. 3 is a diagram for explaining a marker coordinate detecting unit, and FIGS. 4 and 5 are diagrams for explaining a filter application range determining unit.

As shown in FIG. 2, the image processing unit 26 includes a marker coordinate detecting unit 26a, a motion vector calculating unit 26b, a filter application range determining unit 26c, and a filtered image generating unit 26d.

The marker coordinate detecting unit 26a detects coordinates of the stent markers attached to the balloon of the stent with the balloon for each of a plurality of X-ray images (fluoroscopic images) in a time sequence stored in the image data storing unit 25.

Figure 3:
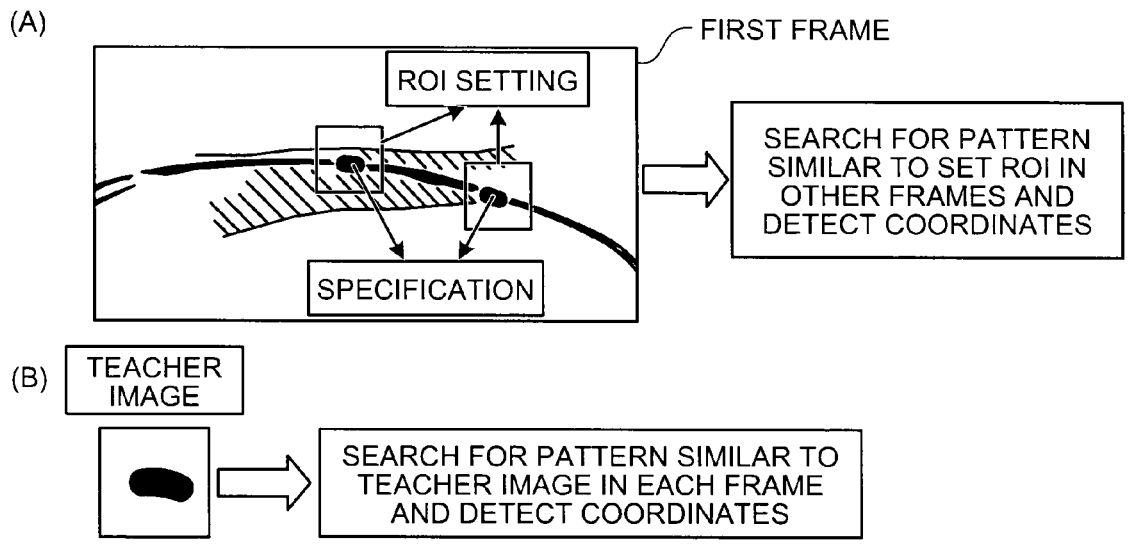
FIG. 3 is a diagram for explaining a marker coordinate detecting unit.

For example, the system control unit 21 controls to display a first generated X-ray image (first frame) on the monitor of the display unit 23 as shown in (A) in FIG. 3 among the X-ray images in a time sequence stored in the image data storing unit 25.

A doctor who sees the first frame specifies the two stent markers in the first frame via the input unit 22 as shown in (A) in FIG. 3. Whereby, the marker coordinate detecting unit 26a detects coordinates of each of the two stent markers in the first frame.

Thereafter, as shown in (A) in FIG. 3, the marker coordinate detecting unit 26a sets rectangles each having a center at the coordinates of a corresponding one of the two stent markers specified in the first frame as a region of interest (ROI), searches for a pattern that is similar to a pattern in the set ROI in the second and other subsequent frames, for example, by a cross-correlation method, and detects coordinates at which the cross correlation value is the highest as coordinates of the stent marker.

In (A) in FIG. 3, explanation is given for the case where a doctor specifies two stent markers; however, the present invention is not limited thereto, and a doctor can specify one stent marker. In this case, the marker coordinate detecting unit 26a performs the cross-correlation method using the ROI set based on the coordinates of the specified stent marker to detect coordinates of another stent marker in the first frame.

Moreover, coordinates of the stent marker can be detected by a method explained below. That is, the marker coordinate detecting unit 26a detects coordinates of the stent marker by using a teacher image indicating characteristics such a shape and a brightness that the stent marker attached to the stent actually used in the treatment includes in an X-ray image.

For example, as shown in (B) in FIG. 3, an X-ray image of the stent marker is separately stored as a teacher image, and the marker coordinate detecting unit 26a searches for a pattern similar to the teacher image in each frame. Then, the marker coordinate detecting unit 26a detects coordinates of the stent marker by detecting coordinates in a region having the highest similarity from searched candidate regions of the stent marker.

Returning to FIG. 2, the motion vector calculating unit 26b sets the first frame of the X-ray images as a reference image, and the coordinates of the stent markers detected by the marker coordinate detecting unit 26a in the first frame as reference coordinates. Then, the motion vector calculating unit 26b compares the coordinates of the stent markers detected by the marker coordinate detecting unit 26a in each of the X-ray images of the second and subsequent frames with the reference coordinates.

Whereby, the motion vector calculating unit 26b calculates a motion vector of the coordinates of the stent markers in each of the second and subsequent frames with respect to the reference coordinates.

For example, when the first frame is radiographed at a time "T=t0", the second frame is radiographed at a time "T=t1", and the third frame is radiographed at a time "T=t2", the motion vector calculating unit 26b compares the coordinates of the stent markers in the second frame with the coordinates (reference coordinates) of the stent markers in the first frame to calculate the motion vector of the second frame as a "vector V1". In the similar manner, the motion vector calculating unit 26b compares the coordinates of the stent markers in the third frame with the reference coordinates to calculate the motion vector of the third frame as a "vector V2".

The filter application range determining unit 26c moves and determines an application range of a recursive filter that is a smoothing filter used for noise reduction in each X-ray image based on the motion vector calculated by the motion vector calculating unit 26b.

The recursive filter is a filter that reduces noise of a process target image by adding to pixel values of pixels constituting an X-ray image (process target image) as a process target the values that are obtained by performing a predetermined weighting on pixel values of pixels constituting a reference image that is an X-ray image (past frame) generated before the process target image. In other words, the recursive filter reduces noise of the process target image by using pixel values of corresponding pixels (with the same coordinates) in the process target image and the reference image.

However, when the stent moves due to heartbeats, the position of the stent in an X-ray image moves in a time sequence, so that if the application range is fixed when performing the noise reducing process on the second frame by using the first frame or performing the noise reducing process on the third frame by using the second frame, motion blur occurs. That is, as shown in FIG. 4, if the range of applying the recursive filter (application range) is fixed (i.e., if the same coordinate axis is used for all of the frames), a different object is exposed between a pixel of the process target image and a pixel of the reference image in the same coordinates.

Therefore, the filter application range determining unit 26c moves the application range of the recursive filter in each frame by a coordinate transformation and determines the application range based on the motion vector calculated by the motion vector calculating unit 26b. Specifically, the filter application range determining unit 26c moves the application range by moving the coordinate axis of each of the second frame and the third frame by the coordinate transformation as shown in FIG. 5 based on the motion vector (vector V1 and vector V2). Examples of the above described coordinate transformation include processes such as a parallel movement, a rotation movement, and an affine transformation. The application range of the recursive filter specifically has a size explained below. For example, if the image size is "1000× 1000", the filter application range determining unit 26c sets the size of the application range of the recursive filter to "3×3" to "30×30" and moves the application range based on the motion vector. For example, the filter application range determining unit 26c sets the size of the application range of the recursive filter to "9×9" and moves the application range based on the motion vector.

Whereby, as shown in FIG. 5, the same object is exposed between a pixel of the process target image and a pixel of the reference image in the same coordinates in the coordinate axis after the movement.

Returning to FIG. 3, the filtered image generating unit 26d performs a process by the recursive filter between the application ranges determined by the filter application range determining unit 26c in the process target image and the reference image to generate a filtered image based on the reference image from the process target image.

Specifically, the filtered image generating unit 26d generates a filtered image by adding values that are obtained by performing a predetermined weighting on pixel values of the reference image to pixel values of the process target image for corresponding pixels between the application ranges of the process target image and the reference image.

The system control unit 21 controls to sequentially display filtered images generated in order by the filtered image generating unit 26d on the monitor of the display unit 23 in a time sequence.

Figure 6:
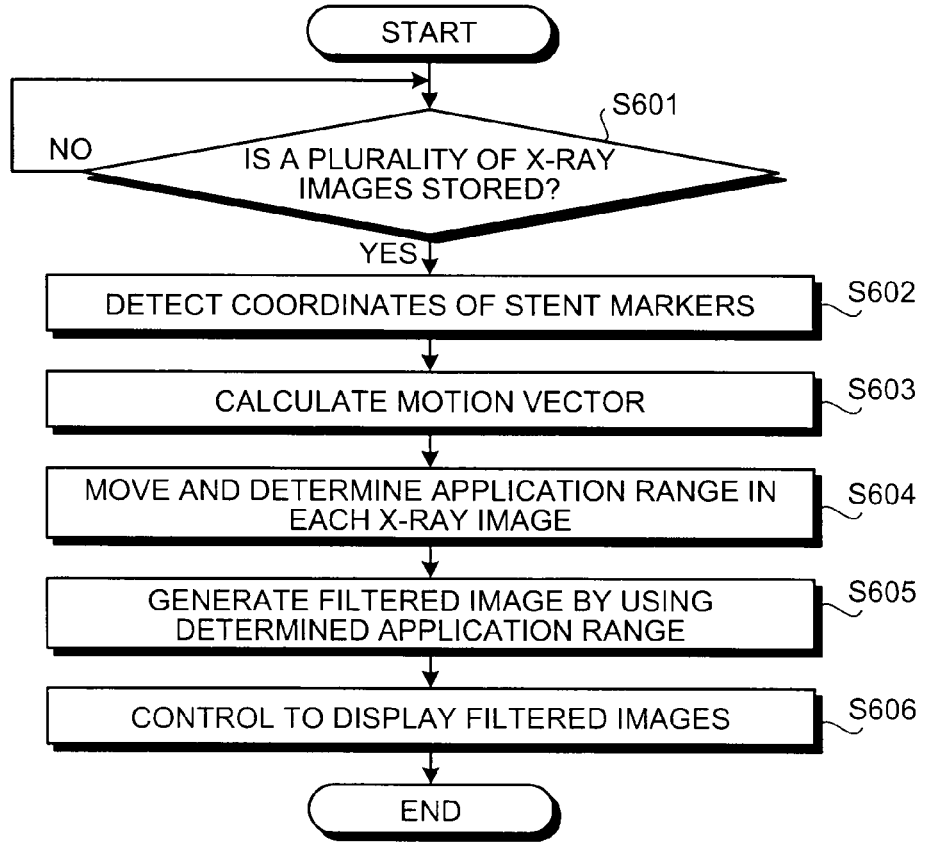
FIG. 6 is a flowchart for explaining a process in the X-ray diagnosis apparatus according to the first embodiment.

Next, the process in the X-ray diagnosis apparatus 100 in the first embodiment is explained with reference to FIG. 6. FIG. 6 is a flowchart for explaining the process in the X-ray diagnosis apparatus according to the first embodiment.

As shown in FIG. 6, in the X-ray diagnosis apparatus 100 in the first embodiment, when a fluoroscopic radiography of an X-ray image for an infarct site of the subject P in which the stent is inserted is started and a plurality of X-ray images in a time sequence is stored in the image data storing unit 25 (Yes at Step S601), the marker coordinate detecting unit 26a detects the coordinates of the stent markers in each X-ray image (Step S602, see FIG. 3).

Then, the motion vector calculating unit 26b, with the coordinates of the stent markers detected in the reference image (first frame) as the reference coordinates, calculates the motion vector of the coordinates of the stent markers detected in each X-ray image of the second and subsequent frames with respect to the reference coordinates (Step S603).

Next, the filter application range determining unit 26c moves and determines the application range of the recursive filter in each X-ray image based on the motion vector calculated by the motion vector calculating unit 26b (Step S604, see FIG. 4).

Thereafter, the filtered image generating unit 26d generates a filtered image by using the application range determined by the filter application range determining unit 26c (Step S605). Specifically, the filter application range determining unit 26c generates the filtered image based on the reference image from the process target image by performing the process by the recursive filter between the application ranges determined in the process target image and the reference image.

Then, the system control unit 21 controls to sequentially display the filtered images generated in order by the filtered image generating unit 26d on the monitor of the display unit 23 in a time sequence (Step S606), and the process ends.

As described above, in the first embodiment, when a plurality of X-ray images in a time sequence is stored in the image data storing unit 25, the marker coordinate detecting unit 26a detects the coordinates of the stent markers in each x-ray image, and the motion vector calculating unit 26b, with the coordinates of the stent markers detected in the reference image (first frame) as the reference coordinates, calculates the motion vector of the coordinates of the stent markers detected in each X-ray image of the second and subsequent frames with respect to the reference coordinates.

Then, the filter application range determining unit 26c moves and determines the application range of the recursive filter in each X-ray image based on the motion vector calculated by the motion vector calculating unit 26b, and the filtered image generating unit 26d performs a process by the recursive filter between the application ranges determined in the process target image and the reference image to generate a filtered image based on the reference image from the process target image. Then, the system control unit 21 controls to sequentially display filtered images generated in order by the filtered image generating unit 26d on the monitor of the display unit 23 in a time sequence.

Therefore, even when radiographing an organ that moves such as a heart, it is possible to prevent motion blur from occurring due to the recursive filter that uses information on the past frame (reference image) by moving the application range, so that, as the main characteristics described above, the noise reducing effect by the smoothing filter (recursive filter) can be always ensured. Moreover, conventionally, when the noise reducing process is performed based on the position of a marker, a process of transforming a whole image is performed together with the filtering process. However, in the first embodiment, the noise reduction is performed only by the filtering process in which the application range is moved, so that the processing speed can be increased and furthermore image distortion that may occur due to the image transformation can be prevented.

In the first embodiment, explanation is given for the case where the process target of the smoothing filter is an X-ray image as an original image. In a second embodiment, explanation is given for the case where the process target of the smoothing filter is a high-frequency component image separated from an original image.

Figure 7:
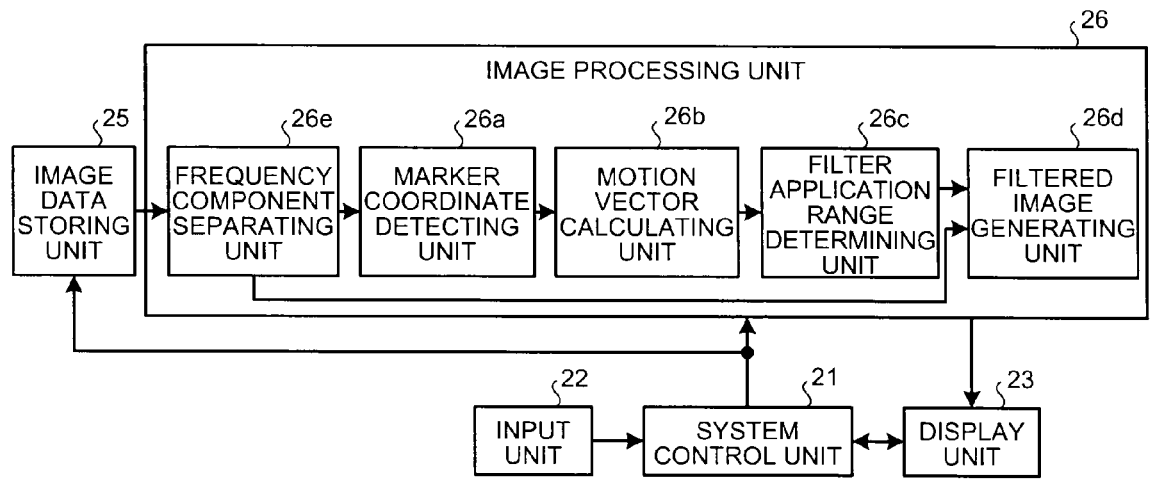
FIG. 7 is a diagram for explaining a configuration of an image processing unit according to a second embodiment.

First, a configuration of the image processing unit 26 according to the second embodiment is explained with reference to FIG. 7. FIG. 7 is a diagram for explaining the configuration of the image processing unit according to the second embodiment.

The X-ray diagnosis apparatus 100 in the second embodiment has the similar configuration to the X-ray diagnosis apparatus 100 in the first embodiment shown in FIG. 1. However, as shown in FIG. 7, the image processing unit 26 in the second embodiment additionally includes a frequency component separating unit 26e compared with the image processing unit 26 in the first embodiment shown in FIG. 2, and the process contents of the marker coordinate detecting unit 26a, the motion vector calculating unit 26b, the filter application range determining unit 26c, and the filtered image generating unit 26d are different from those in the first embodiment. The difference from the first embodiment is mainly explained below.

In clinical practice in which the intravascular interventional treatment is performed, it is important to improve the visibility by reducing the noise of a peripheral area including a stent as a moving object in an X-ray image. On the other hand, it is not important compared with the peripheral area including the stent to improve the visibility of a background object (for example, a lung, a diaphragm, and the like) of which movement is low compared with a heart other than the stent.

The moving object such as the stent is included in the high-frequency component of an X-ray image, and the background object is included in the low-frequency component of an X-ray image. Therefore, the frequency component separating unit 26e shown in FIG. 7 separates each of a plurality of X-ray images into a high-frequency component image and a low-frequency component image.

The marker coordinate detecting unit 26a in the second embodiment performs the process of detecting the coordinates of the stent markers on the high-frequency component image separated from an original image by the frequency component separating unit 26e.

The motion vector calculating unit 26b in the second embodiment performs the process of calculating the motion vector by using the coordinates of the stent markers in the high-frequency component image detected by the marker coordinate detecting unit 26a. In other words, the motion vector calculating unit 26b in the second embodiment calculates, with the coordinates of the stent markers detected in the high-frequency component image in the first frame as the reference coordinates, the motion vector of the coordinates of the stent markers detected in each high-frequency component image in the second and subsequent frames with respect to the reference coordinates.

The filter application range determining unit 26c in the second embodiment performs the process (i.e., moving process of the coordinate axis) of determining the application range by using the motion vector in the high-frequency component image calculated by the motion vector calculating unit 26b.

The filtered image generating unit 26d in the second embodiment generates a filtered image by applying the recursive filter between the application ranges in the high-frequency component images of the reference image and the process target image and combining with the low-frequency component image of the process target image. In other words, the filtered image generating unit 26d generates the filtered image by combining a stent image of which noise is reduced and an image of the background object.

Figure 8:
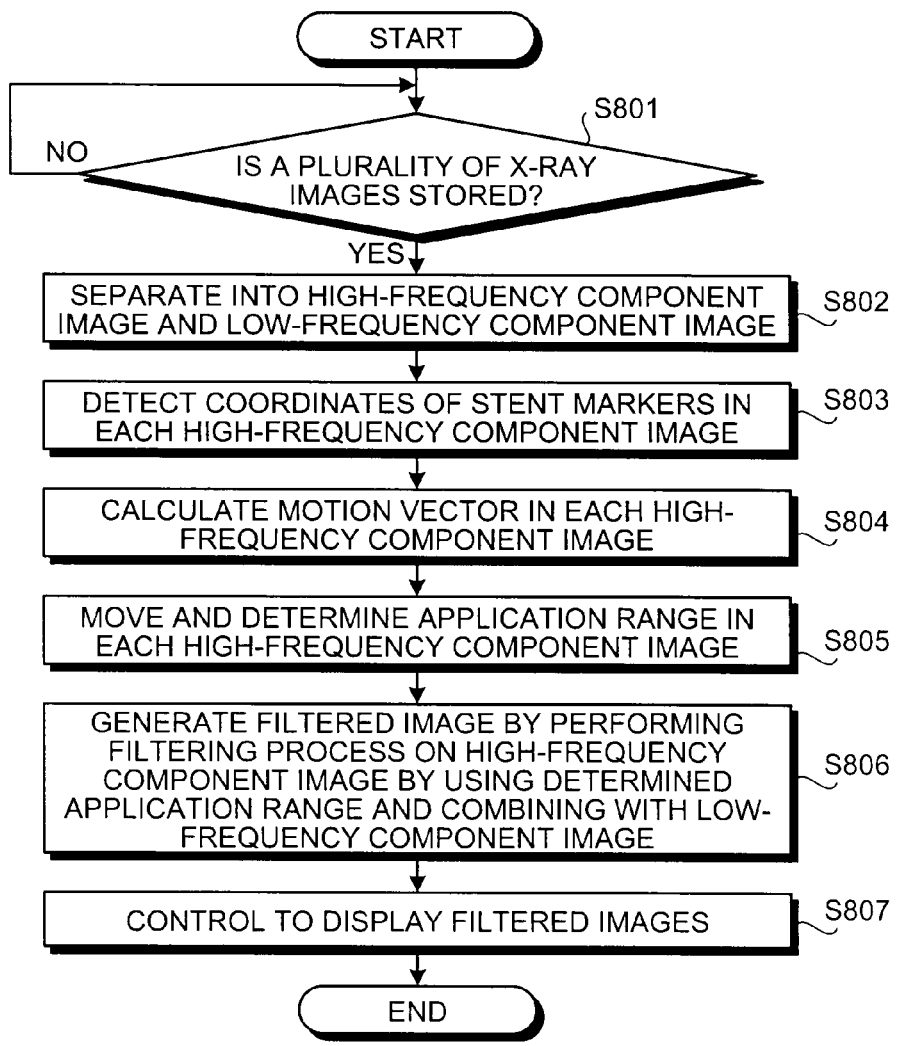
FIG. 8 is a flowchart for explaining a process of an X-ray diagnosis apparatus according to the second embodiment.

Next, the process in the X-ray diagnosis apparatus 100 in the second embodiment is explained with reference to FIG. 8. FIG. 8 is a flowchart for explaining the process in the X-ray diagnosis apparatus according to the second embodiment.

As shown in FIG. 8, in the X-ray diagnosis apparatus 100 in the second embodiment, when a fluoroscopic radiography of an X-ray image for an infarct site of the subject P in which the stent is inserted is started and a plurality of X-ray images in a time sequence is stored in the image data storing unit 25 (Yes at Step S801), the frequency component separating unit 26e separates each X-ray image into the high-frequency component image and the low-frequency component image (Step S802).

Then, the marker coordinate detecting unit 26a detects the coordinates of the stent markers in the high-frequency component image separated from each X-ray image (Step S803).

Next, the motion vector calculating unit 26b calculates the motion vector in each high-frequency component image of the second and subsequent frames (Step S804).

Thereafter, the filter application range determining unit 26c moves and determines the application range of the recursive filter in each high-frequency component image based on the motion vector calculated by the motion vector calculating unit 26b (Step S805).

Moreover, the filtered image generating unit 26d generates the filtered image by performing the filtering process by the recursive filter on the high-frequency component image by using the application range determined by the filter application range determining unit 26c and combining with the low-frequency component image (Step S806).

Then, the system control unit 21 controls to sequentially display the filtered images generated in order by the filtered image generating unit 26d on the monitor of the display unit 23 in a time sequence (Step S807), and the process ends.

As described above, in the second embodiment, a treatment action by a doctor who performs the intravascular interventional treatment can be smoothly performed by surely reducing the noise by moving the application range only for a moving object such a stent.

In the present embodiment, explanation is give for the case where the image processing on the low-frequency component image is not performed; however, the present invention is not limited thereto. For example, it is possible to perform the image processing of suppressing the contrast on the low-frequency component image and combining with the high-frequency component image on which the recursive filtering process is performed.

Figure 9:
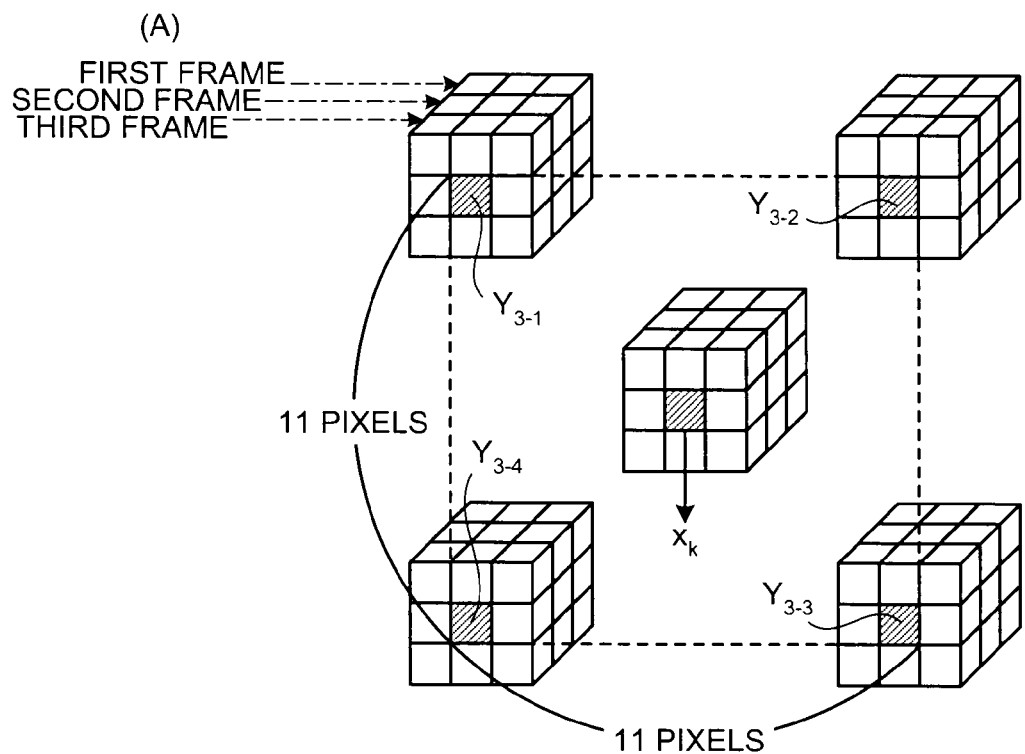
FIGS. 9 and 10 are diagrams for explaining a filtered image generating unit according to a third embodiment.
Figure 9:
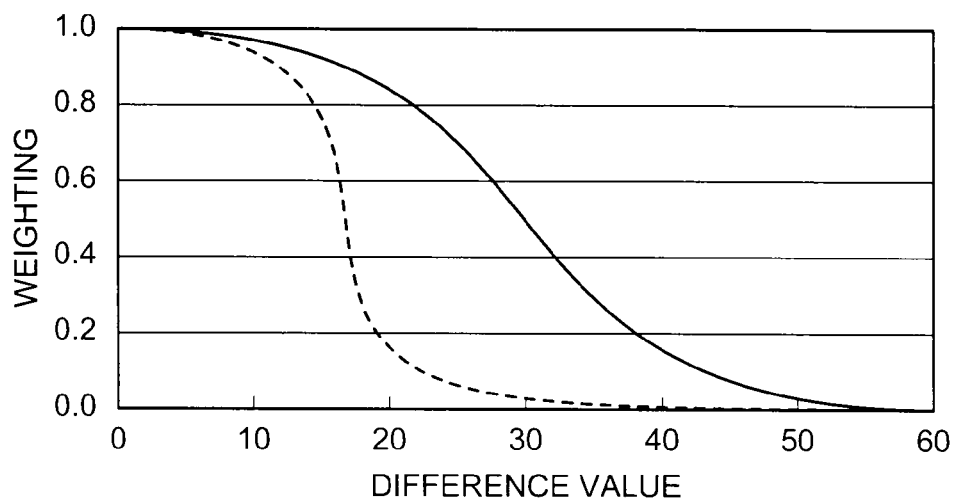
Figure 10:
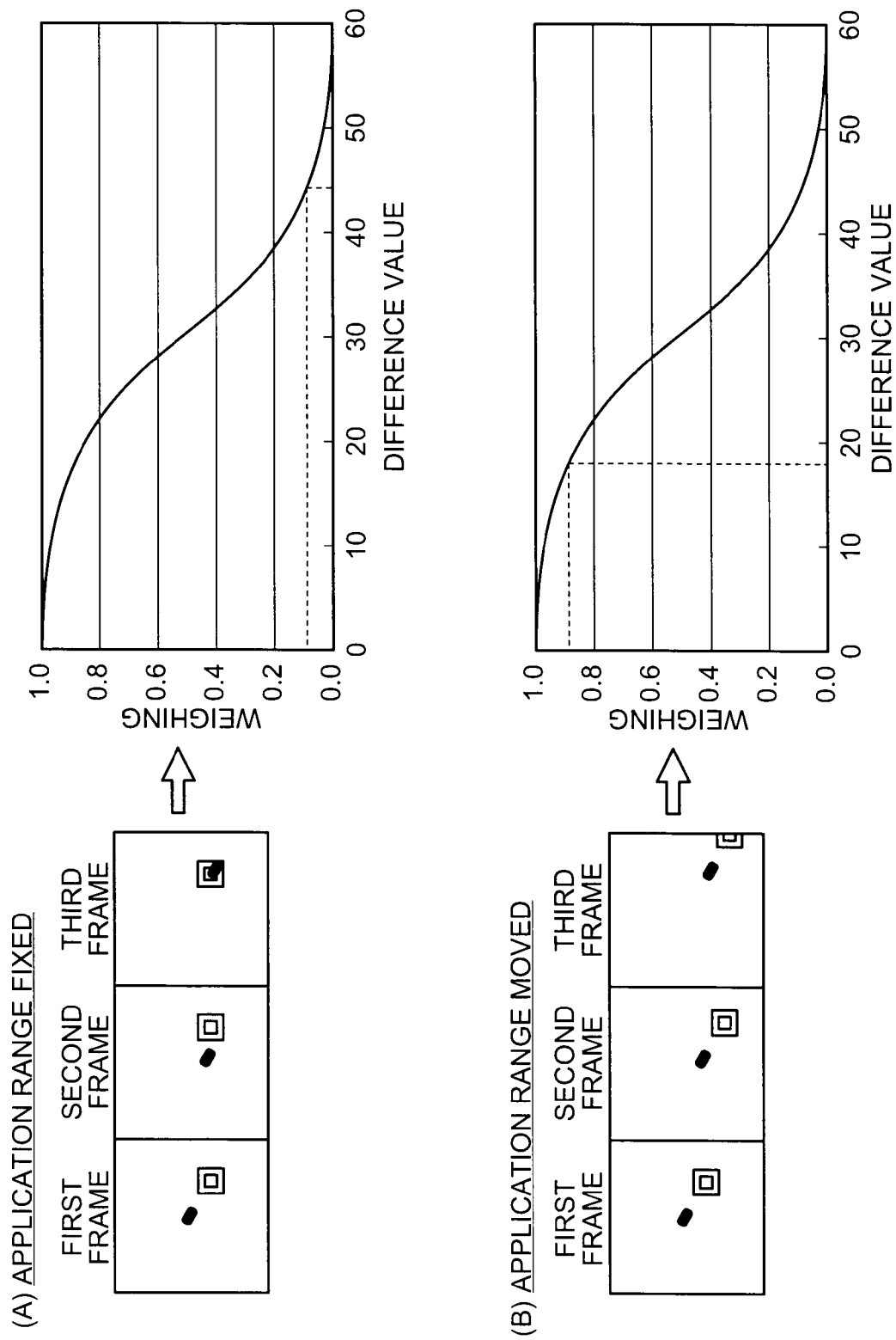

In a third embodiment, explanation is given for the case of performing the noise reducing process with reference to FIG. 9 and FIG. 10, which is different from the first and second embodiments. FIGS. 9 and 10 are diagrams for explaining a filtered image generating unit according to the third embodiment.

The filtered image generating unit 26d in the third embodiment performs the noise reducing process using a spatial filter described in "Nambu K, Iseki H. A noise reduction method based on a statistical test of high dimensional pixel vectors for dynamic and volumetric images. Riv Neuroradiol 2005; 18:21-33." and "Nishiki, Method for reducing noise in X-ray images by averaging pixels based on the normalized difference with the relevant pixel, Radiological Physics and Technology, Vol 2, 2008" after the application range determining process by the filter application range determining unit 26c is performed.

Specifically, the filtered image generating unit 26d calculates the difference value between each pixel in the process target image and pixels in a predetermined range in a spatial direction by using pixel values of pixels corresponding to the process target image in the application range of the reference image. Then, the filtered image generating unit 26d newly calculates a pixel value of each pixel of the process target image by changing the weighting of each pixel in the process target image in accordance with the size of the calculated difference value and generates the filtered image.

Specifically, first, the filtered image generating unit 26d in the third embodiment calculates the difference value between pixel values of a process target pixel of the process target image and each pixel of a peripheral pixel group around the process target pixel in the same space (in the process target image). At this time, the filtered image generating unit 26d calculates the difference value while taking pixel values of pixels in the same coordinates in the application ranges in a time sequence direction into consideration.

For example, when the third frame is the process target image, the filtered image generating unit 26d sets the first frame and the second frame as the reference images, and superimposes the first frame, the second frame, and the third frame as shown in (A) in FIG. 9 according to the coordinates and calculates the difference value between pixel values of a process target pixel "$X_3$" of the third frame and a pixel "$Y_{3-1}$" of the peripheral pixel group in the following manner.

As shown in (A) in FIG. 9, the filtered image generating unit 26d calculates the difference value between the pixel "$X_3$" and the pixel "$Y_{3-1}$" from the pixel value of each of 27 pixels in total in the spatial direction and the time sequence direction in a "3 pixels×3 pixels×3 pixels" with the pixel "$X_3$" as a center and the pixel value of each of 27 pixels in total in the spatial direction and the time sequence direction in a "3 pixels×3 pixels×3 pixels" with the pixel "$Y_{3-1}$" as a center.

In the similar manner, as shown in (A) in FIG. 9, the filtered image generating unit 26d calculates the difference value between the pixel "$X_3$" of the third frame and each pixel of the "peripheral pixel group (121 pixels) included in a "11 pixels× 11 pixels" surrounded by the pixel "$Y_{3-1}$", a pixel "$Y_{3-2}$", a pixel "$Y_{3-3}$", and a pixel "$Y_{3-4}$"" based on the pixel values of 27 pixels in total in the spatial direction and the time sequence direction. In other words, the filtered image generating unit 26d even calculates the difference value from the pixel "$X_3$" itself by using pixels corresponding to the first and second frames.

Then, as shown in (B) in FIG. 9, the filtered image generating unit 26d obtains a "weighting" corresponding to the difference value calculated for each of the 121 pixels including the pixel "$X_3$" in the third frame by a "weighting" that is preset to correspond to the difference value. Then, the filtered image generating unit 26d multiples a pixel value of each pixel by the obtained weighting and calculates a total value, and divides the "total value of the pixel values after the weighting" by the "total value of the weighting", to calculate a new pixel value of the pixel "$X_3$", thereby generating a filtered image in which the noise is reduced from the third frame. The value of the "weighting" corresponding to the difference value can be changed arbitrary by an administrator of the X-ray diagnosis apparatus 100 (for example, see a solid line and a dotted line illustrated in (B) in FIG. 9).

It is explained that the application range determining process by the filter application range determining unit 26c is needed also in the spatial filtering process by the filtered image generating unit 26d. When the stent moves due to heartbeats, as shown in (A) in FIG. 10, if the application range of the spatial filter is fixed (if the same coordinate axis is used for all of the frames), a different object is exposed between a pixel of the process target image and a pixel of the reference image in the same coordinates.

In other words, if the application range of the spatial filter is fixed, even when the difference value is calculated by using pixel values of pixels different in a time sequence in a predetermined range (for example, the above described range of 11 pixels×11 pixels) in the spatial direction, the same object does not present at the same position (coordinates) of the last frame (first and second frames), and consequently the difference value becomes large. Therefore, as shown in (A) in FIG. 10, the weighting becomes small and thus the smoothing is not performed, so that the noise cannot be reduced.

Therefore, in the third embodiment also, the filtered image generating unit 26d uses the application range that is moved based on the motion vector by the filter application range determining unit 26c so that the same object presents at the same coordinates in each frame as shown in (B) in FIG. 10. Thus, for example, even when an object (stent) in an image moves due to heartbeats, the filtered image generating unit 26d surely makes the difference value of a "similar area" small in each frame as shown in (B) in FIG. 10 and performs the smoothing process with an appropriate weighting to reduce the noise of the process target image.

The process in the X-ray diagnosis apparatus 100 in the third embodiment is different from the process in the X-ray diagnosis apparatus 100 in the first embodiment explained with reference to FIG. 6 only in the point that the smoothing filter used at Step S605 is the spatial filter, so that explanation thereof is omitted. Moreover, in the similar manner to the first embodiment, the application range of the spatial filter specifically has a size explained below. For example, if the image size is "1000×1000", the filter application range determining unit 26c sets the size of the application range of the spatial filter to "3×3" to "30×30" and moves the application range based on the motion vector. For example, the filter application range determining unit 26c sets the size of the application range of the spatial filter to "9×9" and moves the application range based on the motion vector.

Moreover, in the third embodiment, as explained in the second embodiment, it is possible to separate an original image into the high-frequency component image and the low-frequency component image and perform the process by the spatial filter only on the high-frequency component image.

As described above, in the third embodiment, even in the case of using the spatial filter that generates a filtered image only from pixel values of pixels constituting the process target image using weighting corresponding to a difference value calculated by using the reference image (past frame), the noise reducing effect can be always ensured. Moreover, in the third embodiment also, the noise reduction is performed only by the filtering process in which the application range is moved, so that the processing speed can be increased and furthermore image distortion that may occur due to the image transformation that is performed in the conventional filtering process can be prevented in the similar manner to the first embodiment.

In the first to third embodiments, explanation is given for the case of performing the smoothing filter process on an X-ray image generated by the fluoroscopic radiography; however, the present invention is not limited thereto, and it is possible to perform the smoothing filter process on an X-ray image generated by a typical radiography in which an X dosage is larger than in the fluoroscopic radiography.

Moreover, in the first to third embodiments, explanation is given for the case where the image processing unit 26 is embedded in the X-ray diagnosis apparatus 100; however, the present invention is not limited thereto. The image processing unit 26 can be arranged independently from the X-ray diagnosis apparatus 100. In this case, the image processing unit 26 performs the smoothing filter process on an X-ray image received from the X-ray diagnosis apparatus 100. Furthermore, the image processing unit 26 can perform the smoothing filter process on X-ray images received from a plurality of the X-ray diagnosis apparatuses. An X-ray image as the process target by the image processing unit 26 can be an X-ray image generated by an X-ray computed tomography (CT) apparatus. Moreover, an image as the process target by the image processing unit 26 can be a medical image such as a magnetic resonance image (MRI) generated by an MRI apparatus and an ultrasound image generated by an ultrasound diagnosis apparatus.

Furthermore, in the first to third embodiments, explanation is given for the case of moving the application range of the smoothing filter by using the stent markers; however, the present invention is not limited thereto, and the application range of the smoothing filter can be moved by using a different object as a marker.

For example, a tip portion of a guide wire that is used when inserting a whole stent or a catheter of the stent, a marker wire, or the like can be detected as marker coordinates to move the application range of the smoothing filter.

Moreover, in the first to third embodiments, explanation is given for the case of the interventional treatment as the treatment performed with reference to an X-ray image and using a stent as a treatment equipment; however, the present invention can be applied to an equipment for treatment used in various treatments performed with reference to an X-ray image.

For example, when an electrode of an electrophysiological catheter that is used for performing a treatment for arrhythmia, a drill of a rotablator that is used for performing a treatment for a hard infarct site that is difficult to expand with a balloon, a metal cylinder with holes configured to be attached on a tip end of a catheter that is used for performing a treatment for directional coronary arterectomy, a catheter with an ultrasound-wave transmitting-receiving function for checking a situation inside a blood vessel of an infarct portion, or the like is used as a marker, the present invention can be applied to the treatments in which these equipments for treatment are used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An X-ray diagnosis apparatus, comprising:
an image data generating unit configured to generate X-ray images in a time sequence by detecting, with a detector, an X-ray that is radiated from an X-ray tube and is transmitted through a subject;

a processor configured to detect a position of an X-ray impermeable feature point included in a treatment equipment for an interventional treatment from at least a first image and a second image included in the X-ray images generated in a time sequence by the image data generating unit, determine an application range of a smoothing filter in the first image and the second image based on the detected position of the feature point in the first image and the detected position of the feature point in the second image, and perform a smoothing filter process by using the first image and the second image based on the determined application range of the smoothing filter.

2. The X-ray diagnosis apparatus according to claim 1, wherein the processor is further configured to separate each of the X-ray images into a high-frequency component image and a low-frequency component image, perform a position detecting process of the feature point and a determining process of the application range on the high-frequency component images, and perform the smoothing filter process between application ranges in high-frequency component images of the first image and the second image and combine with a corresponding low-frequency component image.

3. The X-ray diagnosis apparatus according to claim 2, wherein the processor is further configured to perform a smoothing filter process of adding to a pixel value of an image as a process target a value that is obtained by performing a predetermined weighting on a pixel value of an image other than the process target for a corresponding pixel between application ranges of the first image and the second image.

4. The X-ray diagnosis apparatus according to claim 2, wherein the processor is further configured to calculate a difference value between a pixel value of a pixel in a predetermined range in a spatial direction in an image to be a process target and a pixel value of a corresponding pixel in an image other than the process target between application ranges of the first image and the second image, and perform a smoothing filter process of calculating a new pixel value by changing weighting of each pixel in the image to be the process target in accordance with a size of calculated difference value.

5. The X-ray diagnosis apparatus according to claim 1, wherein the processor is further configured to perform a smoothing filter process of adding to a pixel value of an image as a process target a value that is obtained by performing a predetermined weighting on a pixel value of an image other than the process target for a corresponding pixel between application ranges of the first image and the second image.

6. The X-ray diagnosis apparatus according to claim 1, wherein the processor is further configured to calculate a difference value between a pixel value of a pixel in a predetermined range in a spatial direction in an image to be a process target and a pixel value of a corresponding pixel in an image other than the process target between application ranges of the first image and the second image, and perform a smoothing filter process of calculating a new pixel value by changing weighting of each pixel in the image to be the process target in accordance with a size of calculated difference value.

7. An image processing apparatus, comprising:

a processor configured to detect a position of an X-ray impermeable feature point included in a treatment equipment for an interventional treatment from at least a first image and a second image included in a plurality of medical images generated in a time sequence, determine an application range of a smoothing filter in the first image and the second image based on the detected position of the feature point in the first image and the detected position of the feature point in the second image, and perform a smoothing filter process by using the first image and the second image based on the determined application range of the smoothing filter.

* * * * *